United States Patent [19]
Singer et al.

[11] 3,950,365
[45] Apr. 13, 1976

[54] METHOD FOR PURIFICATION OF FATTY ACID MIXTURES

[75] Inventors: Helmut Singer, Mainz-Gonsenheim; Werner Stein, Erkrath-Unterbach, both of Germany

[73] Assignee: Henkel & Cie G.m.b.H., Dusseldorf-Holthausen, Germany

[22] Filed: Nov. 30, 1973

[21] Appl. No.: 420,436

[30] Foreign Application Priority Data
Dec. 14, 1972  Germany............................ 2261067

[52] U.S. Cl. ................ 260/419; 260/97.5; 260/407
[51] Int. Cl.² ... C11C 1/08; C11C 3/00; C09F 7/06; C08H 5/00
[58] Field of Search.................... 260/419, 407, 97.5

[56] References Cited
UNITED STATES PATENTS
3,367,952   2/1968   Arit, Jr. ............................. 260/407
3,627,708  12/1971   Morse .............................. 260/2.2 R OTHER PUBLICATIONS
*Advances in Polymer Science* (5 Band, 2 Heft) Springer–Uerlag Berlin, Heidelberg, New York 1967 Article 4,2,3,3 pp. 190–191.
*Amber–Hi–Lites*, Special Issue, Jan. 1971 Macroreticular Amberlyst Ion Exchange Resins.

*Primary Examiner*—Patrick P. Garvin
*Assistant Examiner*—P. E. Konopka
*Attorney, Agent, or Firm*—Hammond & Littell

[57] ABSTRACT

A method for the purification of mixtures of fatty acids or fatty acid esters containing polyunsaturated components by heating the mixture in the presence of an organic macroporous, acid ion exchange resin having a specific surface area of at least 35 m²/gm and devoid of gel characteristics, and then separating the purified mixture by distillation. The method is especially useful for the production of oleic acid which is relatively free of linoleic acid.

9 Claims, No Drawings

METHOD FOR PURIFICATION OF FATTY ACID MIXTURES

THE PRIOR ART

Several methods are already known for separating monounsaturated fatty acids or fatty acid esters from polyunsaturated fatty acids or fatty acid esters. Thus, technical oleic acid can be separated from polyunsaturated fatty acids, especially linoleic acid, by low-temperature crystallization from acetone or methanol at −60°C. Separation can also be achieved by using the urea complex reaction. This involves adding the fatty acid mixtures to be processed in the form of their methyl esters. These methods of separation are relatively expensive, however.

On the other hand, it is known to render harmless the polyunsaturated components present in fatty acid mixtures used as raw material for obtaining olein, and which spoil the Mackey test for oleins, by means of polymerization. Polymerization reactions for purification purposes can only be performed in a purely thermal fashion, however, i.e., in the absence of the catalysts which are usually added for this purpose, since such catalysts as Lewis acids and acid clays act simultaneously as dehydration catalysts and, in a mechanism which is not yet completely understood, the monounsaturated fatty acids can also participate in the polymerization reaction. A purely thermal polymerization, which would enable a significant removal of the polyunsaturated components, must be carried out at temperatures of approximately 300°C and above, if necessary under pressure as well. Such extreme reaction conditions, however, lead to side reactions, especially decarboxylizations.

OBJECTS OF THE INVENTION

An object of the present invention is the development of a method for separation of small amounts of polyunsaturated components from mixtures of fatty acids or fatty acid esters while avoiding the above drawbacks.

Another object of the present invention is the development of a method for the separation of polyunsaturated components from mixtures of higher fatty acid compounds consisting essentially of heating a mixture of higher fatty acid compounds selected from the group consisting of higher fatty acids and esters thereof with alkanols having 1 to 4 carbon atoms and glycerol, said mixture containing a major amount of mono-unsaturated higher fatty acid compounds and from 3% to 25% by weight of polyunsaturated higher fatty acid compounds, to a temperature of between 90°C and 150°C in the presence of an organic macroporous, acid ion exchange resin having a specific surface area of at least 35 m²/gm and devoid of gel characteristics, for a time sufficient to lower to the desired value the amount of polyunsaturated higher fatty acid compounds in said mixture, distilling and recovering said mixture of fatty acid compounds substantially free of polyunsaturated components.

These and other objects of the present invention will become apparent as the description thereof proceeds.

DESCRIPTION OF THE INVENTION

The present invention relates to a process for purifying fatty acid mixtures or fatty acid ester mixtures from higher polyunsaturated fatty acid or ester components.

It has been discovered that the above-described disadvantages of the prior art in the purification of fatty acid mixtures or fatty acid ester mixtures from higher polyunsaturated fatty acid or ester components can be obviated by a method which is characterized in that the mixtures are heated to temperatures from 90°C to 150°C, preferably 100°C to 130°C in the presence of an organic macroporous acid ion exchange resin without a gelling characteristic and having a high specific surface area of at least 35 m²/gm, and are subsequently separated by distillation. The polyunsaturated components in the mixture undergo dimerization the trimerization which greatly increase their boiling points.

More particularly, the invention relates to a method for the separation of polyunsaturated components from mixtures of higher fatty acid compounds consisting essentially of heating a mixture of higher fatty acid compounds selected from the group consisting of higher fatty acids and esters thereof with alkanols having 1 to 4 carbon atoms and glycerol, said mixture containing a major amount of mono-unsaturated higher fatty acid compounds, from 3% to 25% by weight of polyunsaturated higher fatty acid compounds, to a temperature of between 90°C and 150°C in the presence of an organic macroporous, acid ion exchange resin having a specific surface are of at least 35 m²/gm and devoid of gel characteristics, a time sufficient to lower to the desired value the amount of polyunsaturated higher fatty acid compounds in said mixture, distilling and recovering said mixture of fatty acid compounds substantially free of polyunsaturated components.

The organic macroporous acid ion exchange resins are defined as resins devoid of gel characteristics and having an average pore width of 250 A to 300 A or a porosity of approximately 0.3 ml/ml. For example, a value of at least 35 m²gm, preferably 40 m²/gm is to be regarded as a high specific surface area. Such ion exchange resins can be produced by conventional sulfonation of styrene-divinylbenzene copolymers which have been obtained by suspension polymerization. Some of the properties of these ion exchange resins, and their use as catalysts for the synthesis of tert-butylmethacrylate from isobutylene and methacrylic acid, are described in the Journal of the American Chemical Society, 84 (1962), pages 305 to 306. For example, macroporous acid ion exchange resins of this type are commercially available under the Registered Trade Mark "Amberlyst-15". Amberlyst 15 is the trade name for very highly purified sulfonation products of styrene-divinylbenzene copolymers. This product has a surface area of 42.5 m²/gm, an apparent density of 1.012 gm/ml, a true skeletal density of 1.513 gm/ml, a porosity of 0.319 ml/ml and an average diameter of the pores of 288 A.

The quantity of catalyst to be used is generally between 2% and 15% by weight, preferably 3% to 10% by weight. The particular quantity to be used depends upon the amount of polyunsaturated acid, or linoleic acid, present in the starting material and upon the desired reaction time. Catalyst concentrations of less than 2% by weight also produce commercially acceptable results although, in this case, the reaction times are very long. The upper limit of the given amounts of catalyst can be exceeded, if particularly short reaction times are desired.

During the conversion, the ion exchange resin catalyst undergoes no significant loss of activity and may be reused several times without any special activation measures being necessary. In addition, due to its grandular structure the catalyst is readily separated from the reaction mixture. Furthermore, due to this fact, it is a simple matter to remove residues of the product from the catalyst by washing. It is possible to use conventional organic solvents, particularly petroleum ether or higher boiling benzine fractions, as well as aromatic hydrocarbons, alcohols or acetic acid.

The reaction times in the method according to the invention are generally between 2 hours and 10 hours. Generally reaction times of between 3 and 4 hours do not need to be exceeded.

The purification method according to the invention can be carried out particularly advantageously in a continuous operation. In this case, reactors mounted vertically, for example, can be charged with the catalyst according to the invention, brought to the desired reaction temperature by external heating, and the raw material (preheated if necessary) can be fed into the catalyst at a rate corresponding to the rate at which it emerges from the reactor. The reactor volume is then selected to give the desired residence time (reaction time). With continuous refinements of the method, recycling the product mixture or additional throughput is not necessary in correctly dimensioned reactors.

The method according to the invention can be used for all mixtures of higher fatty acids or higher fatty acid esters having a polyunsaturated component content of less than 30%; that is of between 3% to 25% by weight of the mixture. The amount of saturated components in the mixture can be widely varied without effecting the results. However, for best results, it is preferable to make a rough separation of the unsaturated components from the saturated components of fatty acids or esters before employing the process of the invention on the unsaturated components. These mixtures of higher fatty acids or higher fatty acid esters of the unsaturated component usually contain from 0% to 30% by weight of saturated components, from 55% to 97% by weight of mono-unsaturated components and from 3% to 25% by weight, preferably from 5% to 20% by weight, of polyunsaturated components. In each instance, the unsaturation is in the fatty acid moiety when a fatty acid ester is employed. The higher fatty acids are aliphatic hydrocarbon monocarboxylic acids having 8 to 26 carbon atoms and a terminal carboxyl group. If mixtures of esters are to be purified, the process involves primarily esters of the lower alcohols containing 1 to 4 carbon atoms, such as the alkanols having 1 to 4 carbon atoms, particularly methanol. However, mono-, di- and triglycerides can be purified in the manner described, in the presence of inert organic solvents if necessary.

Both mixtures of naturally-occurring higher carboxylic acids and their esters, as well as mixtures of synthetic higher carboxylic acids and their esters, can be subjected to the purification method in accordance with the invention, therefore arbitrarily produced mixtures will be covered by this definition of mixtures of higher fatty acids.

The use of the method of the invention for the purification of technical oleic acid and natural fatty acid mixtures rich in oleic acid, such as olive oil-fatty acids, palm oil-fatty acids and peanut oil-fatty acids, all of which can also be used in the form of their esters, is of particular interest.

No special preliminary purification of the raw material, especially preliminary drying, is necessary.

The above-mentioned mixtures are heated to the abovementioned temperatures in the charging operation after addition of the catalyst and kept at this temperature until the content of polyunsaturated components of the higher fatty acid mixture has dropped to the desired level. The reaction time is a function of the amount of catalyst, reaction temperature and content of polyunsaturated components in the mixture and must be determined empirically by sampling.

When the reaction is complete, the catalyst is removed by coarse filtration and may be reused at once. The mixture of products separated from the catalyst is separated by distillation into the unchanged monounsaturated and saturated fatty acids or their esters as distillate, and the dimerized or trimerized components as the still bottoms. The latter substances are also valuable products, especially in the area of synthetic resins and polyesters.

The considerable advantage that can be gained by the method according to the invention can be seen from the fact that it is possible with its aid, and with surprisingly high selectivity and very mild conditions, working with mixtures of higher fatty acids or higher fatty acid esters with contents of 3% to 25% of polyunsaturated mixture components, to dimerize or trimerize primarily the latter and thus make simple separation by means of distillation possible.

The following examples are merely illustrative of the present invention without being deemed limitative in any manner thereof.

EXAMPLES 1 to 5

The contents of the monounsaturated and the polyunsaturated monomeric components given in the following examples were determined by gaschromatographic separation. The content of dimers and trimers was determined by molecular distillation wherein the boiling point of the dimers at 0.02 mm Hg was up to 290°C after previously separating the monomers by distillation wherein the boiling point at 0.1 mm Hg was up to 220°C.

The starting material was a mixture of the methyl esters of higher fatty acids having a content of 71% to 74% of oleic acid, 7% to 10% of linoleic acid and the remainder of saturated fatty acids with 14 to 18 carbon atoms. The catalyst was "Amberlyst-15".

The reaction conditions and results are shown in Table I below.

TABLE I

| Example No. | Amount of Esters | Amount of Catalyst | Time in Hours | Temp. | Monomer Fraction | 1st Distillate Linoleic Acid in the Monomer Fraction | Oleic Acid in the Monomer Fraction | Dimers + Trimers |
| --- | --- | --- | --- | --- | --- | --- | --- | --- |
| | gm | gm | | °C | % | % | % | % |
| 1 | 30 | 3 | 3 | 120 | 94 | 1.0 | 82 | 6 |
| 2 | 30 | 2 | 2 | 120 | 95 | 1.5 | 74 | 5 |

TABLE I-continued

| Example No. | Amount of Esters gm | Amount of Catalyst gm | Time in Hours | Temp. °C | Monomer Fraction % | 1st Distillate Linoleic Acid in the Monomer Fraction % | Oleic Acid in the Monomer Fraction % | Dimers + Trimers % |
|---|---|---|---|---|---|---|---|---|
| 3 | 150 | 20 | 3 | 120 | 93 | 1.0 | 78 | 5 2 |
| 4 | 30 | 4 | 5 | 100 | 90 | 1.0 | 77 | 10 |
| 5 | 30 | 1 | 2 | 150 | 96 | 1.4 | 75 | 4 |

EXAMPLE 6

The methyl esters of the mixed fatty acids used in Examples 1 to 5 were fed, on a continuous process basis at a rate of 20 ml/hr, into a reaction tube having a length of 25 cm and having an internal diameter of 1 cm and which was filled with 8 gm Amberlyst-15. The tube was maintained at a temperature of 100°C by external heating.

The reaction product comprised 77% of methyl oleate and contained 2.5% of residual linoleic acid ester and 6% of dimeric and trimeric products. The remainder comprised monomeric saturated components.

EXAMPLES 7 to 12

Starting material:
Fatty acid mixture having 71% to 74% of oleic acid, 8% to 10% of linoleic acid, and the remainder, saturated $C_{14}$ to $C_{18}$ fatty acids.
Catalyst: Amberlyst-15
The experimental conditions and results are given in Table II.

TABLE II

| Example No. | Amount of Acid gm | Amount of Catalyst gm | Time in Hours | Temp. °C | Monomer Fraction % | 1st Distillate Linoleic Acid in the Monomer Fraction % | Oleic Acid in the Monomer Fraction % | Dimers and Trimers % |
|---|---|---|---|---|---|---|---|---|
| 7 | 30 | 2 | 4 | 125 | 92 | 2.2 | 75 | 8 |
| 8 | 90 | 9 | 6 | 110 | 89 | 1.0 | 79 | 11 |
| 9 | 30 | 2 | 3 | 120 | 90 | 1.0 | 78 | 10 |
| 10 | 50 | 2 | 6 | 120 | 97 | 2.0 | 76 | 3 |
| 11 | 90 | 6* | 2 | 120 | 97 | 1.0 | 70 | 3 |
| 12 | 200 | 8* | 7 | 120 | 92 | 2.2 | 78 | 8 |

*in the presence of 4 gm $H_2O$

EXAMPLE 13

A. 90 gm of the acid mixture used in Examples 7 to 12 were heated to 120°C for 2 hours after adding 6 gm Amberlyst-15R. The reaction product mixture consisted of 90% monomers and 10% dimers and trimers. The monomers had a residual linoleic acid content of 1.2% and an oleic acid content of 72%.

B. 90 gm of said acid mixture was again added to the catalyst which had been separated by coarse filtration, and the experiment was repeated. The resultant product mixture comprised 94% monomers and 6% dimers and trimers. The monomers contained 1.0% residual linoleic acid and 73% oleic acid.

From the above examples (A) and (B) it can be seen that the catalyst of the present invention may be recycled and reused several times without any intermediate reactivation, while still providing a very effective separation.

EXAMPLES 14 to 19

The starting materials used were:
A Fatty acid methylester mixture having 55% oleic acid, 19% linoleic acid and 26% saturated $C_{14}$ to $C_{18}$ fatty acids.
B Fatty acids methylester mixture having 71% oleic acid, 5% linoleic acid and 24% saturated $C_{14}$ to $C_{18}$ fatty acids.
C Fatty acid mixture having 55% oleic acid, 19% linoleic acid and 26% saturated $C_{14}$ to $C_{18}$ fatty acids.
D. Fatty acid mixture having 72% oleic acid, 5% linoleic acid and 23% saturated $C_{14}$ to $C_{18}$ fatty acids.

The catalyst was Amberlyst-15. The experimental conditions and results are shown in Table III.

TABLE III

| Example No. | Starting Material | Amount gm | Amount of Catalyst gm | Time in Huors | Temp. °C | Monomer Fraction % | 1st Distillate Linoleic Acid in the Monomer Fraction % | Oleic Acid in the Monomer Fraction % | Dimers and Trimers % |
|---|---|---|---|---|---|---|---|---|---|
| 14 | A | 30 | 3 | 3 | 120 | 84 | 1.5 | 64 | 16 |
| 15 | A | 30 | 3 | 5 | 120 | 83 | 0.5 | 67 | 17 |
| 16 | B | 30 | 3 | 5 | 120 | 93 | 1.0 | 71 | 7 |
| 17 | B | 30 | 2 | 3 | 120 | 94 | 0.5 | 75 | 6 |
| 18 | C | 90 | 6 | 5 | 120 | 90 | 0.2 | 57 | 10 |

TABLE III-continued

| Example No. | Starting Material | Amount gm | Amount of Catalyst gm | Time in Huors | Temp. °C | Monomer Fraction % | 1st Distillate Linoleic Acid in the Monomer Fraction % | Oleic Acid in the Monomer Fraction % | Dimers and Trimers |
|---|---|---|---|---|---|---|---|---|---|
| 19 | D | 200 | 8 | 4 | 120 | 91 | 0.5 | 74 | 9 |

Although the present invention has been disclosed in connection with a few preferred embodiments thereof, variations and modifications may be resorted to by those skilled in the art without departing from the principles of the new invention. All of these variations and modifications are considered to be within the true spirit and scope of the present invention as disclosed in the foregoing description and defined by the appended claims.

We claim:

1. A method for the separation of polyunsaturated components from mixtures of higher fatty acid compounds, wherein the fatty acids thereof have 8 to 26 carbon atoms consisting essentially of heating a mixture of higher fatty acid compounds selected from the group consisting of higher fatty acids and esters thereof with alkanols having 1 to 4 carbon atoms and glycerol, said mixture comprising a major amount of monounsaturated higher fatty acid compounds and from 3% to 25% by weight of polyunsaturated higher fatty acid compounds, to a temperature of between 90°C and 150°C in the presence of from 2% to 15% by weight based upon the weight of said mixture of an organic macroporous, acid ion exchange resin catalyst devoid of gel characteristics and having a specific surface area of at least 35 $m^2/gm$, said catalyst being the sulfonation product of styrene-divinylbenzene copolymers which have been prepared by suspension polymerization for a time of from 2 to 10 hours wherein said time is sufficient to lower to the desired value the amount of polyunsaturated higher fatty acid compounds in said mixture, separating said ion exchange resin catalyst from said mixture, distilling and recovering said mixture of fatty acid compounds substantially free of polyunsaturated components.

2. The method of claim 1, wherein said temperature employed is between 100°C to 130°C.

3. The method of claim 1, wherein said specific surface area of said organic macroporous catalyst is about 40 $m^2/gm$ and said catalyst has pores with a width of between 250 A to 300 A.

4. The method of claim 1, wherein said catalyst is used in amounts of from 3% to 10% by weight based upon the weight of said mixture.

5. The method of claim 1, wherein said mixture comprises from 55% to 95% by weight of monounsaturated higher fatty acid compounds, from 5% to 20% by weight of polyunsaturated higher fatty acid compounds and from 0% to 30% by weight of saturated higher fatty acid compounds.

6. The method of claim 1, wherein said time of heating is from 3 to 4 hours.

7. The method of claim 1, wherein said mixture of higher fatty acid compounds is technical oleic acid or its methyl ester.

8. The method of claim 1, wherein said mixture of higher fatty acid compounds is a naturally-occurring fatty acid mixture rich in oleic acid or its methyl ester.

9. The method of claim 1, wherein said mixture of higher fatty acid compounds is a mixture of esters of said higher fatty acids with alkanols having 1 to 4 carbon atoms.

* * * * *